(12) United States Patent
Mylari et al.

(10) Patent No.: US 7,973,073 B2
(45) Date of Patent: Jul. 5, 2011

(54) ANTIDIABETIC AGENT FOR CONTROL OF DIABETIC HYPERGLYCEMIA AND DIABETIC COMPLICATIONS

(75) Inventors: Banavara L. Mylari, East Lyme, CT (US); Mary E. Vaman Rao, Hopkinton, MA (US)

(73) Assignee: Indigene Pharmaceuticals, Inc., Westborough, MA (US)

( * ) Notice: Subject to any disclaimer, the term of this patent is extended or adjusted under 35 U.S.C. 154(b) by 664 days.

(21) Appl. No.: 11/818,909

(22) Filed: Jun. 14, 2007

(65) Prior Publication Data

US 2007/0293562 A1 Dec. 20, 2007

Related U.S. Application Data

(60) Provisional application No. 60/814,250, filed on Jun. 16, 2006.

(51) Int. Cl.
*A61K 31/385* (2006.01)
*C07D 339/04* (2006.01)

(52) U.S. Cl. .......................................... 514/440; 549/39

(58) Field of Classification Search ................. 514/440; 549/39
See application file for complete search history.

(56) References Cited

U.S. PATENT DOCUMENTS

| 6,572,888 | B2 | 6/2003 | Byrd |
| 2001/0028896 | A1 | 10/2001 | Byrd |
| 2003/0078269 | A1 | 4/2003 | Pearson et al. |
| 2003/0220301 | A1 | 11/2003 | Lal et al. |
| 2003/0228362 | A1 | 12/2003 | Byrd |
| 2005/0182029 | A1 | 8/2005 | Lal |

FOREIGN PATENT DOCUMENTS

| FR | 2 796 551 A1 | 1/2001 |
| WO | WO-99/61004 A1 | 12/1999 |
| WO | WO-03/068209 A1 | 8/2003 |
| WO | WO-2005/039539 A1 | 5/2005 |

OTHER PUBLICATIONS

International Search Report from PCT/US2007/014034, mailed Dec. 3, 2007.
Carlson et al., "The Plasma Pharmacokinetics of R-(+)-Lipoate to Healthy Human Subjects", *Alternative Medicine Review*, 12:(4)343-351 (2007).

*Primary Examiner* — Taofiq A Solola
(74) *Attorney, Agent, or Firm* — Ropes & Gray LLP (57) ABSTRACT

Described herein is a compound of Formula I, which is the metformin salt of the naturally occurring endogenous biological compound, (R)-(+) α lipoic acid, pharmaceutical compositions containing the compound of Formula I, and methods of treatment of diabetes or diabetic complications with the compound of Formula I.

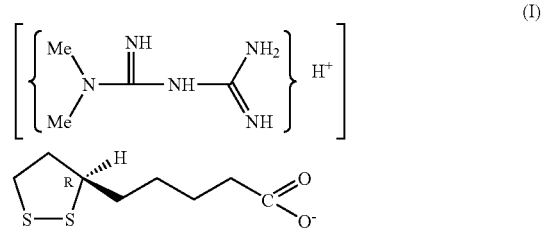

14 Claims, 4 Drawing Sheets

ANTIDIABETIC AGENT FOR CONTROL OF DIABETIC HYPERGLYCEMIA AND DIABETIC COMPLICATIONS

RELATED APPLICATIONS

This application claims the benefit of U.S. Provisional Application No. 60/814,250, filed Jun. 16, 2006. The contents of this application are incorporated herein by reference in its entirety.

BACKGROUND OF THE INVENTION

Diabetes mellitus has become pandemic and according to a forecast by the World Health Organization, there will be a sharp increase in the number of diabetic patients by the year 2030. This is an ominous forecast, because managing the long-term complications of diabetes, which include nephropathy, neuropathy, retinopathy, and cardiovascular complications, will have a serious impact on public health budgets. The hallmark of diabetes is chronically elevated blood glucose levels. It is also known that abnormally elevated glucose levels have an adverse impact on glutathione levels in key diabetic tissues. Furthermore, increased oxidative stress and increased production of reactive oxygen species are implicated under hyperglycemic conditions.

In spite of the early discovery of insulin and its subsequent widespread use in the treatment of diabetes, and the later discovery of and use of sulfonylureas, and thiazolidenediones, such as troglitazone, rosiglitazone or pioglitazone, as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can either have side effects limiting their use, or an agent may not be effective with a particular patient. In the case of insulin dependent diabetes mellitus (Type I), insulin administration usually constitutes the primary course of therapy.

Metformin is a known compound approved by the U.S. Food & Drug Administration for the therapeutic treatment of diabetes. The compound and its preparation and use are disclosed, for example, in U.S. Pat. No. 3,174,901. Metformin is orally effective in the treatment of type 2 diabetes. Metformin (N,N-dimethylimidodicarbonimidic diamide) is a biguanide, anti-hyperglycemic agent currently marketed in the United States in the form of its hydrochloride salt 1,1-dimethylbiguanide hydrochloride.

According to United Kingdom Perspective Diabetes Study (UKPDS) (Clarke et al. *Diabetologia,* 2005, 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with Type 2 diabetes. However, many diabetic patients develop resistance to metformin.

Alpha-lipoic acid has a variety of names, including thioctic acid, 1,2-dithiolane-3-pentanoic acid; 1,2-ditholane-3-valeric acid; 6,8-thioctic acid; 5-[3-C1,2-dithiolanyl)]-pentanoic acid; delta-[3-(1,2-dithiacyclopentyl)] pentanoic acid; acetate replacing factor and pyruvate oxidation factor. Alpha-Lipoic acid has an asymmetric carbon atom and is usually employed in the form of a racemic mixture of its R- and S-enantiomers, particularly in nutritional supplements. All published clinical trials, including those in diabetic patients, have thus far been conducted with racemic alpha-lipoic acid.

Alpha-Lipoic acid, hereafter referred to as lipoic acid, is an antioxidant and is a scavenger of reactive oxygen species (ROS). It chelates metals and recycles endogenous antioxidants. Lipoic acid can scavenge singlet oxygen, $H_2O_2$, hydroxyl radical, NO, and $ONOO^-$. The reduced form of lipoic acid, dihydrolipoic acid, can further scavenge $O_2^-$, and peroxy radicals. Lipoic acid can also chelate several divalent cations, e.g., $Mn^{2+}$, $Cu^{2+}$, $Zn^{2+}$, $Cd^{2+}$, $Pb^{2+}$. Therefore, lipoic acid can inhibit ascorbate-induced production of $H_2O_2$ by $Cu^{2+}$. Lipoic acid can recycle endogenous antioxidants, such as glutathione (GSH) and vitamin C. GSH protects tissues from oxidative stress. Lipoic acid can also affect circulating plasma levels of lactate and pyruvate in diabetic patients. Estrada et al. (*Diabetes,* 1996, 45, 1798-1804) report that lipoic acid induces GLUT transporters and glucose uptake and this suggests that lipoic acid may also stimulate the insulin signaling pathway. Lipoic acid administration has been shown to be active in oxidative stress models including in ischemia-reperfusion injury model. Furthermore, lipoic acid can function as a redox regulator of thiredoxin and NF-kappa B transcription factor. Many of the aspects of lipoic acid described herein are included in the review by Smith et al. *Current Medicinal Chemistry,* 2004, 11, 1135-1146.

SUMMARY OF THE INVENTION

This invention describes chemical compositions of metformin R-(+)-lipoate as well as methods for treating diabetes and diabetic complications such as cataracts, cardiomyopathy, nephropathy, neuropathy, and retinopathy. The compounds and compositions of this invention are highly water soluble and may provide high blood levels of metformin R-(+) lipoate, when administered to patients, preferably by oral administration.

The invention relates to a compound having a structure of formula I as shown below, which is metformin R-(+)-lipoate and is meant to include any polymorphs, solvates, and hydrates thereof.

In certain such embodiments, a compound of formula I comprises, (R)-(+)-lipoate and is substantially free of metformin S-(−)-lipoate. In certain such embodiments, a compound of formula I comprises less than 5%, less than 2%, less than 1%, or even less than 0.5% metformin S(−)-lipoate.

In one aspect, the invention relates to metformin (R)-(+)-lipoate in crystalline form and to a method for the manufacture of crystalline metformin R-(+)-lipoate substantially separated from metformin S-(−)-lipoate. In certain embodiments, such a method comprises a) freshly preparing the free base of metformin from a suitable metformin salt; and b) reacting the freshly prepared free base of metformin with R-(+) lipoic acid at a temperature between about 1° C. and about 40° C.

In certain embodiments, the present invention relates to a pharmaceutical composition of the invention comprising compound of formula I and a pharmaceutically-acceptable carrier, vehicle or diluent.

Figure 2:
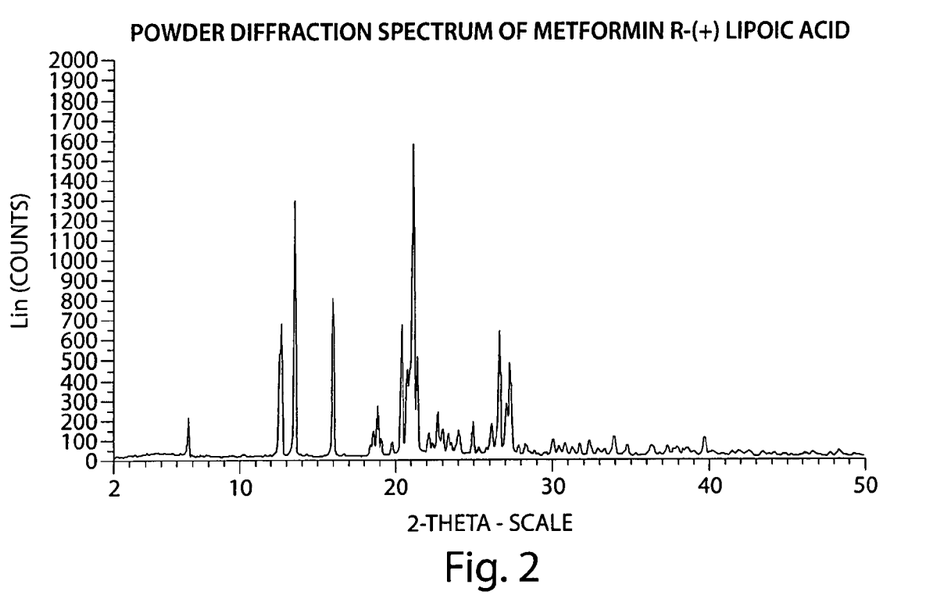
FIG. 2. X-Ray powder diffraction spectrum of metformin R-(+)-lipoate, as described in Example 7.

In certain embodiments, the invention relates to metformin R-(+) lipoate in polymorphic crystalline forms. One such polymorphic form, as characterized in FIG. 2, exhibits essentially the following angle 2-theta values for the peaks having high relative intensities, in a X-ray powder diffraction spectrum:

| Angle 2-Theta | d value [Angstrom] | Relative Intensity [%] |
| --- | --- | --- |
| 13.41 | 6.598 | 100 |
| 15.82 | 5.596 | 24 |
| 20.26 | 4.379 | 69 |
| 20.98 | 4.230 | 97 |
| 22.57 | 3.936 | 19 |
| 26.50 | 3.361 | 22 |
| 27.19 | 3.278 | 47 |

In certain embodiments, the invention relates to a mixture of metformin or a pharmaceutically acceptable salt thereof, (e.g., hydrochloride, succinate, fumarate) with (R)-(+)-lipoic acid, or a pharmaceutically acceptable salt thereof, substantially free from (S)-(−)-lipoic acid. In certain embodiments, the invention relates to a pharmaceutical composition of the invention further comprising a pharmaceutically-acceptable carrier, vehicle or diluent.

In certain embodiments, the present invention relates to a method of treatment of a subject suffering from any of diabetes mellitus (e.g., Type 2 diabetes) and diabetic complications, comprising administering a compound or composition as described herein. Certain aspects of the invention relate to the manufacture of pharmaceutical formulations of the invention for use in the treatment of diabetes mellitus (e.g., Type 2 diabetes) and diabetic complications. In certain embodiments, the invention relates to the use of a solvate or hydrate of a compound or composition of the invention in the treatment of diabetes (e.g., Type 2 diabetes) or diabetic complications.

In certain embodiments, compounds or compositions of the invention may be used in the treatment of diabetes or diabetes complications including, but not limited to, hypertension; micro-angiopathy comprising nephropathy (glomerulosclerosis, albuminuria), retinopathy (microaneurysm, vascular sclerosis, pupille oedema, proliferative retinopathy), cataracts, arteriolosclerosis (peripheral circulatory diseases) and peripheral neuropathy (polynevritis); macro-angiopathy and atherosclerosis comprising coronary disease, myocardial ischemia, angor pectoris, stroke, cerebrovascular disease, myocardial infarction, and peripheral vascular disease (intermittent claudication); and potentially diabetic cataract and diabetic neovascular glaucoma.

In certain embodiments, compounds and compositions as described herein may be used for the treatment of obesity (central/abdominal obesity), insulin resistance, hyperinsulinism, cardio-metabolic syndrome (a high risk of developing a full type 2 diabetes), polycystic ovary syndrome (comprising anovulation, hyperandrogenism, and hirsutism); neuro-degenerative diseases involving Reactive Oxygen Species (ROS) and inflammatory processes (Parkinson, Alzheimer), HIV lipodystrophy (metabolic alterations, including hypertriglyceridemia, diabetic neuropathy, diabetic nephropathy, diabetic retinopathy, cataracts, hyperglycemia, hyperinsulinemia, atherosclerosis, tissue ischemia, particularly myocardial ischemia, cardiac ischemia, diabetic cardiomyopathy, microangiopathy, macroangiopathy, and myocardial infarction.

In certain aspects, the invention relates to a kit comprising: a) a unit dosage form comprising metformin (R)-(+)-lipoate or a unit dosage form comprising combinations of a pharmaceutically acceptable salt of metformin and (R)-(+)-lipoic acid, or a pharmaceutically acceptable salt thereof; b) instructions on how to use the kit; and c) at least one container for holding the unit dosage forms.

In certain such embodiments, the kit is for the treatment of patients with diabetes and/or complications of diabetes.

DETAILED DESCRIPTION OF THE INVENTION

Definitions

The articles "a" and "an" are used herein to refer to one or to more than one (i.e., to at least one) of the grammatical object of the article. By way of example, "an element" means one element or more than one element.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The term "including" is used herein to mean, and is used interchangeably with, the phrase "including but not limited" to.

"Instruction(s)" as used herein means a product label and/or documents describing relevant materials or methodologies pertaining to assembly, preparation, or use of a kit or packaged pharmaceutical. These materials may include any combination of the following: background information, steps or procedures to follow, list of components, proposed dosages, warnings regarding possible side effects, instructions for administering the drug, technical support, and any other related documents.

The term "or" is used herein to mean, and is used interchangeably with, the term "and/or," unless context clearly indicates otherwise.

A "patient" or "subject" is preferably a mammal, such as a human, but can also be a companion animal (e.g., dog, cat, and the like), farm animal (e.g., cow, sheep, pig, horse, and the like) or laboratory animal (e.g., rat, mouse, guinea pig, and the like) in need of treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "solvate" as used herein means a compound of formula I, or a pharmaceutically acceptable salt of a compound of formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "subject in need of treatment for a disorder" is a subject diagnosed with that disorder, likely to develop the disorder, or is suspected of having that disorder. "Substantially free of" as used herein includes, for example, a composition or a compound at least about 70%, at least about 80%, at least about 90%, at least about 95% or at least about 99% free of the indicated compound. For example, metformin R-(+)-alpha-lipoate substantially separated from metformin S-(−)-alpha-lipoate can refer to a composition in which metformin R-(+)-alpha-lipoate makes up at least about 70%, at least about 80%, at least about 90%, at least about 95%, or at least about 99% of the total amount of metformin alpha-lipoate (e.g., the remainder being metformin S-(−)-alpha-lipoate).

The term "such as" is used herein to mean, and is used interchangeably, with the phrase "such as but not limited to".

The term a "sufficient amount" or an "effective amount" of an agent as used herein is that amount sufficient to effect beneficial or desired results, including clinical results, and, as such, an "effective amount" depends upon the context in which it is being applied. For example, in the context of administering an agent that inhibits cancer cell proliferation, an effective amount of an agent is, for example, an amount sufficient to achieve such a reduction in cancer cell proliferation as compared to the response obtained without administration of the agent.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "treat," "treating," or "treatment" as used herein means to counteract a medical condition (e.g., a movement disorder) to the extent that the medical condition is improved according to clinically acceptable standard(s). For example, "to treat a movement disorder" means to improve the movement disorder or relieve symptoms of the particular movement disorder in a patient, wherein the improvement and relief are evaluated with a clinically acceptable standardized test (e.g., a patient self-assessment scale) and/or an empirical test (e.g., PET scan).

A "unit dosage form" is defined herein as a discrete unit that comprises a formulation of a therapeutic agent. Examples of suitable unit dosage forms include, but are not limited to tablets, capsules, or gelcaps.

In certain aspects, the compound formula I is crystalline and has a purity of greater than 95%, greater than 98%, and preferably greater than 99%. In certain embodiments, a compound of formula I in a crystalline form designated hereinafter as polymorph A has advantageous properties including purity, stability, including thermodynamic stability and resistance to moisture in the air (hygroscopicity), and/or bioavailability. Further, polymorph A has favorable handling properties, such that it is advantageously incorporated into pharmaceutical formulations.

The compound of formula I, i.e., metformin (R)-(+)-lipoate can be prepared as follows by dissolving a metformin salt (e.g., hydrochloride, succinate, fumarate, etc.) and lipoic acid in an appropriate inert solvent. In certain embodiments, a suitable solvent for this reaction is methanol. When a pharmaceutically acceptable salt of metformin is employed instead of the free base, a base is added to form the free base of metformin. Suitable bases include alkali and alkali metal hydroxides, alkali and alkali metal carbonates and bicarbonates and tertiary amines. Also included are resin bases. Examples of bases include, but are not limited to, sodium hydroxide, potassium hydroxide, sodium carbonate, potassium carbonate, sodium bicarbonate, potassium bicarbonate, triethyl amine, N-methyl isopropyl amine, and the ion exchange resin amberlyst A26 (OH).

The reaction mixture may be stirred at about ambient temperature to about the refluxing temperature of the solvent being used for about two hours to about six hours, preferably at ambient temperature for about two hours. The salt of formula I may then be isolated from the reaction mixture by methods well known to those skilled in the art and recrystallized from an appropriate solvent or mixture of solvents. Alcohols are preferred solvents for crystallization, preferably methanol.

Hydrates and solvates of the compounds of Formula I of this invention are also included. Chemists and pharmacy scientists of ordinary skill will also recognize that compounds of Formula I of this invention can exist in different polymorphic forms in the solid state.

Metformin hydrochloride can be prepared, for example, as disclosed in *J. Chem. Soc.*, 1922, 121, 1790.

Lipoic acid is commercially available and its synthesis is reported in *Chem. Commun.*, 1986, 1408.

This invention relates to methods of treating diabetes and diabetic complications comprising administering metformin-R-(+)-lipoate. Generally, in carrying out the methods of this invention, an effective dosage for metformin-R-(+)-lipoate is in the range of about 1 mg/kg/day to about 60 mg/kg/day or about 1 mg/kg/day to about 30 mg/kg/day in single or divided doses, preferably 5 mg/kg/day to about 50 mg/kg/day in single or divided doses. When metformin and lipoic acid combinations are used, the dose of metformin is in the range 3 mg/kg/day to about 40 mg/kg/day, and the dose of lipoic acid is 5 mg/kg/day to about 70 mg/kg/day.

As such, these methods disclosed herein include both medical therapeutic (acute) and/or prophylactic (prevention) administration as appropriate. The amount and timing of compounds administered will, of course, be dependent on the subject being treated, on the severity of the affliction, on the manner of administration and on the judgment of the prescribing physician. Thus, because of patient to patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

Therapeutic Compositions

A composition of the present invention may be administered to the subject as a composition which comprises a pharmaceutically effective amount of metformin-R-(+)-lipoate and an acceptable carrier and/or excipients. A pharmaceutically acceptable carrier includes any solvents, dispersion media, or coatings that are physiologically compatible. Preferably, the carrier is suitable for intravenous, intramuscular, oral, intraperitoneal, intradermal, transdermal, topical, or subcutaneous administration. Further, the active compositions of this invention may be administered intranasally, as a rectal suppository or using a "flash" formulation, i.e., allowing the medication to dissolve in the mouth without the need to use water. Furthermore, the active compositions of this invention may be administered to a subject in need of treatment by controlled release dosage forms.

One exemplary pharmaceutically acceptable carrier is physiological saline. Other pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). The composition can be formulated as a solution, microemulsion, liposome, capsule, tablet, or other suitable forms. The pharmaceutical compositions of the present invention are preferably sterile and non-pyrogenic at the time of delivery, and is preferably stable under the conditions of manufacture and storage.

The pharmaceutical compositions formed by combining a composition of the invention and the pharmaceutically acceptable carriers, vehicles or diluents are administered in a variety of dosage forms including any of: tablets, powders, lozenges, syrups, and injectable solutions. These pharmaceutical compositions can further comprise ingredients such as flavorings, binders, and/or excipients. For purposes of oral administration, tablets may comprise various excipients (e.g., sodium citrate, calcium carbonate and calcium phosphate) and/or various disintegrates (e.g., starch, alginic acid and certain complex silicates) with binding agents (e.g., polyvinylpyrrolidone, sucrose, gelatin and acacia). Additionally, lubricating agents (e.g., magnesium stearate, sodium lauryl sulfate and talc) can be used for manufacturing the tablets. Compositions may also be prepared encased in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents, e.g., water, ethanol, propylene glycol, glycerin.

A compound or composition of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO, and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The formulations include, but are not limited to, tablets containing, about 200 mg to about 2000 mg, preferably about 500 mg to about 1000 mg, e.g., 500, 750, 850, or 1000, mg of metformin R-(+)-alpha-lipoate.

Generally, a composition of this invention may be administered orally or parenterally (e.g., intravenous, intramuscular, subcutaneous or intramedullary), however, any other suitable route of administration is contemplated. Topical administration may also be indicated, for example, where the patient is suffering from gastrointestinal disorders or whenever the medication is best applied to the surface of a tissue or organ as determined by the attending physician.

For buccal administration a composition of the invention may take the form of tablets or lozenges formulated in a conventional manner.

For purposes of transdermal (e.g., topical) administration, dilute sterile, aqueous or partially aqueous solutions (usually in about 0.1% to 5% concentration), otherwise similar to the above parenteral solutions, are prepared.

As discussed above, metformin and lipoic acid may be administered separately, such that the invention also includes combined or separate pharmaceutical compositions in kit form. When the metformin and lipoic acid are administered separately, administration may be simultaneous or sequential and may be in any order. In certain embodiments where administration is sequential, they may be administered, for example, within one day, twelve hours, six hours, four hours, two hours, one hour, thirty minutes, ten minutes, or even five minutes of one another.

The kit comprises a container comprising the unit dosage forms, such as a divided bottle or a divided foil packet. Typically the kit comprises directions for the administration of the components. The kit form is particularly advantageous when the components are preferably administered in different dosage forms (e.g., oral and parenteral), are administered at different dosage intervals, or when titration of the individual components of the combination is desired by the prescribing physician.

Another example of such a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

The following examples illustrate particular embodiments of the invention. Examples 1-6 describe procedures for preparing metformin-R-(+)-lipoate. The products of Examples 1-6 were then subject to the procedure of Example 7 to afford the crystalline form of metformin-R-(+)-lipoate with appended characterization (FIGS. 1-4).

Example 1

Preparation of Metformin R-(+)-Lipoate

Step 1.1 Preparation of the Free Base of Metformin

Amberlyst A26 (OH) ion exchange resin (60 g) was washed 3 times with deionized water and twice with 2% (v/v) deionized water in methanol. The resin was loaded into a 2.5 cm diameter glass column (packed column height was 20 cm). The column was flushed further with 300 mL of 2% (v/v) deionized water in methanol. Metformin hydrochloride (6.5 g) was dissolved in 180 ml of 2% (v/v) deionized water in methanol and eluted through the ion exchange column. The column is further washed with 200 mL of 2% (v/v) deionized water in methanol. The combined eluent was concentrated under reduced pressure affording a white powder. The powder was dissolved in acetone, filtered over celite, and the eluent, containing the free base of metformin, concentrated under reduced pressure.
OR
Amberlyst A-26(OH) ion exchange resin (60.097) was mixed with 60 mL of deionized water in a beaker and soaked for 1 hour. The contents of the beaker was transferred into a column (height=25 cm). The packed column was flushed with 100 mL of deionized water at a rate of ~25 mL/min (the eluted solvent is almost colorless; pH is ~6-7). The column was flushed with deionized water (2×100 mL), until the eluted solvent is colorless and pH=~5). Metformin hydrochloride (6.515 g) was dissolved in deionized water 50 mL (pH of the solution is ~7-8) and applied to the column. The column was eluted with deionized water until the pH of the eluted solution was neutral. The eluent was concentrated under reduced pressure at 55° C. to afford off-white solid. The solid was dissolved in acetone (300 mL), filtered and the filtrate evaporated to afford the free base of metformin in the form of a white solid powder.

Step 1.2. Preparation of Metformin R-(+)-Lipoate

Metformin (50 g, in the form of its free base) was placed in a 1 L round bottom flask to which 79.84 g of crystalline (R)-(+)-lipoic acid was added. HPLC grade methanol (750 mL) was added to the flask and the mixture stirred for 2 hours until it became a solution. The solvent was removed on a rotary evaporator under reduced pressure at 40° C. The obtained solid was suspended in water (750 mL) and stirred until completely dissolved. The obtained solution was transferred into two 325 mL flasks and lyophilized for 48 h to afford 129.84 g (100%) of a pale yellow powder. The resulting yellow powder (2.0 g) was dissolved in 20 mL of warm methanol and to this was added acetonitrile dropwise while stirring until the solution became cloudy. Stirring was stopped and the mixture was left at room temperature for 48 h, yielding highly water-soluble, large yellow needles of metformin R-(+)-lipoate; m.p. 134-136° C.; $[\alpha]_D^{25}$=+35.62°; $C_{12}H_{25}N_5O_2S_2$ calculated C 42.99, H 7.46, N 20.89, S 19.10; found C 43.13, H 7.60, N 20.72, S 18.99.

Example 2

Preparation of Metformin R-(+)-Lipoate in Acetone

Metformin, (free base) prepared as described above in Step 1.1, was dissolved in 70 mL of acetone. R-(+)-lipoic acid was dissolved in 10 mL of acetone. The two solutions were combined and stirred for 10 minutes. The resulting precipitate was filtered and the solid residue dried under vacuum to afford metformin R-(+)-lipoate (yield 95%).

Example 3

Preparation of Metformin R-(+)-Lipoate in Acetonitrile

Metformin, (free base) prepared as described above in Step 1.1, was dissolved in 50 mL of acetonitrile. R-(+)-lipoic acid was dissolved in 20 mL of acetonitrile. The two solutions were combined and stirred for 10 minutes. The resulting precipitate was filtered and the solid residue dried under vacuum to afford metformin R-(+)-lipoate (yield 95%).

Example 4

Preparation of Metformin R-(+)-Lipoate

Sodium methoxide (0.31 g) was dissolved in methanol (2 mL) and to this solution was added metformin hydrochloride (1 g) while stirring. The stirring was continued for an additional 10 min. Acetone (40 mL) was then added, stirred for 20 min, and the mixture was filtered. To the filtrate, containing metformin in the form of its free base, R-(+) lipoic acid (1.25 g dissolved in 15 mL acetone) was added dropwise with constant stirring resulting in the precipitation of a pale yellow solid. The mixture was stirred for an additional 20 min and filtered. The light yellow solid was washed with acetone (30 mL), filtered, and dried to yield metformin R-(+)-lipoate; m.p. 148-150° C.; $[\alpha]_D^{20}$=+67.7° (c=1, water); $C_{12}H_{25}N_5O_2S_2$ calculated C 42.99, H 7.46, N 20.89, S 19.10; found C 43.09, H 7.62, N 20.84, S 19.23.

Example 5

Preparation of Metformin R-(+)-Lipoate

To a suspension of metformin hydrochloride (10.06 g) in methanol (400 mL) was added sodium hydroxide (2.23 g)

dissolved in water (5 mL) with constant stirring. The solution was stirred for an additional 20 minutes and then concentrated to afford an off-white solid. The solid was washed with acetone (500 mL), filtered, and to the filtrate was added R-(+) lipoic acid (12.5 g) in of acetone (250 mL) dropwise with constant stirring. Metformin R-(+) lipoate precipitated out during the addition of lipoic acid. The mixture was stirred for an additional 20 minutes. The precipitated metformin R-(+)-lipoate was then filtered. The solid is washed in acetone with stirring for 10 minutes, filtered and dried to obtain metformin R-(+)-lipoate.

Example 6

To a solution of the free base of metformin 2.5 g in acetone (100 mL) was added a solution of R-(+) lipoic acid (4.3 g) in acetone (35 mL) dropwise while stirring. A pale yellow precipitate forms and the mixture is stirred for an additional 30 minutes. The precipitate was filtered and re-suspended in acetone with stirring for 10 minutes. It was then filtered and dried to obtain metformin R-(+)-lipoate.

The products of Examples 1 through 6 may be further purified by recrystallization. For example, acetonitrile or acetone may be added to a solution of metformin R-(+)-lipoic acid in water or methanol until it becomes turbid and then placed into a refrigerator at 4° C. whereupon fine needles are formed. Alternatively, for example, tetrahydrofuran or ethyl acetate may be added to a solution of metformin R-(+) lipoate in methanol until it becomes turbid, or n-hexane may be added to a solution of metformin R-(+) lipoic acid in absolute ethanol until it becomes turbid. A specific exemplification of the purification procedure is included in Example 7.

Example 7

Figure 3:
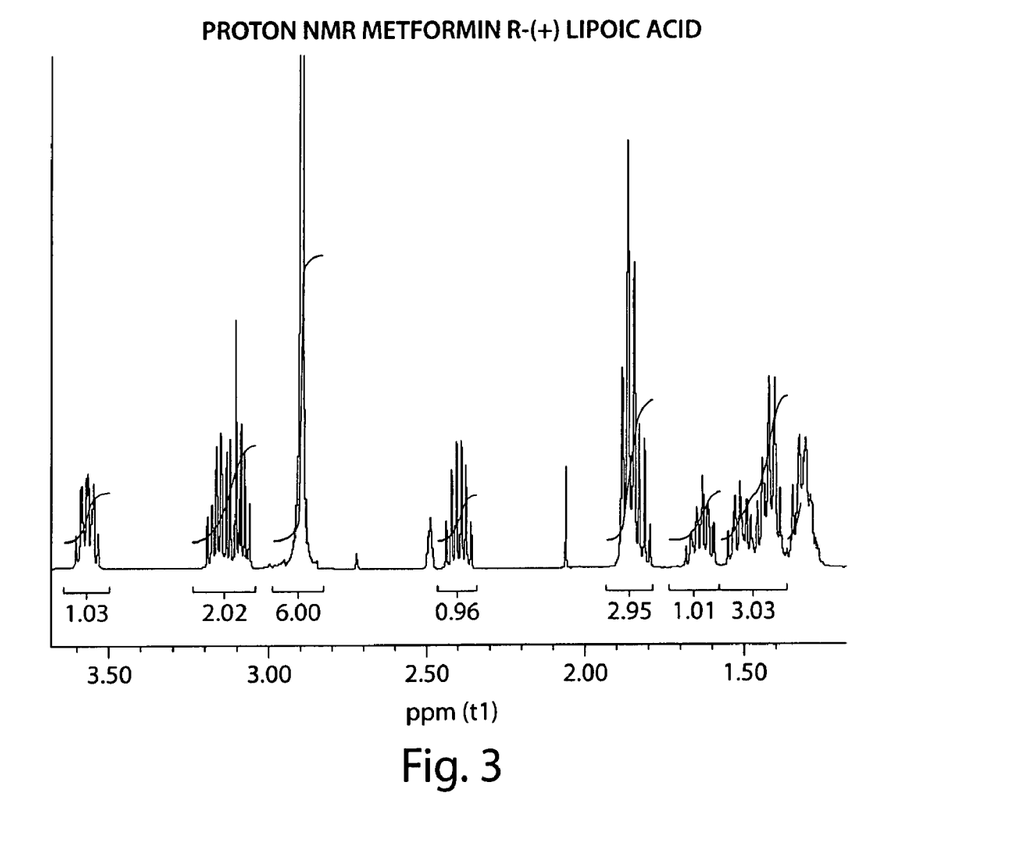
FIG. 3. $^1$H NMR of metformin R-(+)-lipoate, as described in Example 7.
Figure 4:
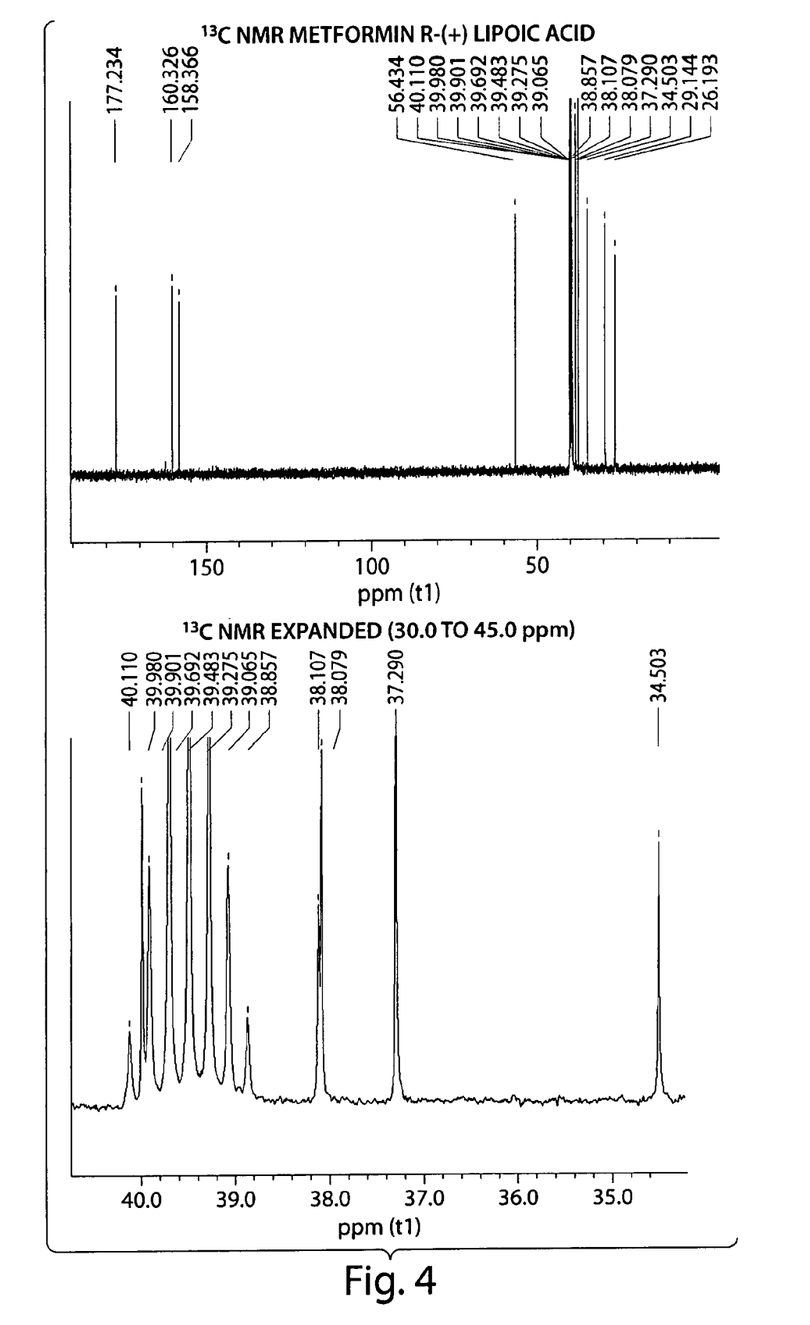
FIG. 4. $^{13}$C NMR of metformin R-(+)-lipoate, as described in Example 7.

Metformin R-(+)-lipoate (250 mg) was dissolved in water (1.2 mL). Acetonitrile was added slowly to this solution with a continuous vortex mixer. Initially addition of acetonitrile produces slight turbidity, but becomes clear when vortexed. Acetonitrile was added (100 mL of acetonitrile) until a semi-permanent turbidity appears that upon further stirring becomes a clear solution. The solution was left undisturbed in the refrigerator at 4° C. for 10-15 hours. Fine crystalline needles are filtered, dried and analyzed: mp 150-152° C.; specific rotation: 60-65 (c=1 in water; at 20° C. & 589 nm); $^1$H NMR, (FIG. 3); $^{13}$C NMR, (FIG. 4); DSC; onset at 153.88° C., peak at 156.03° C.; crystal structure depicted in (FIG. 1) (details given below); powder diffraction X-ray spectrum depicted in (FIG. 2) (Start: 2.000°-End: 49.997-Step: 0.005 0-Step time: 10.3 s-Anode: Cu-WL 1:1.5406-Creation: 23.05.2007 14:30:31 Operations: Smooth 0.085 I Background 0.000,0.000 I Import)

Figure 1:
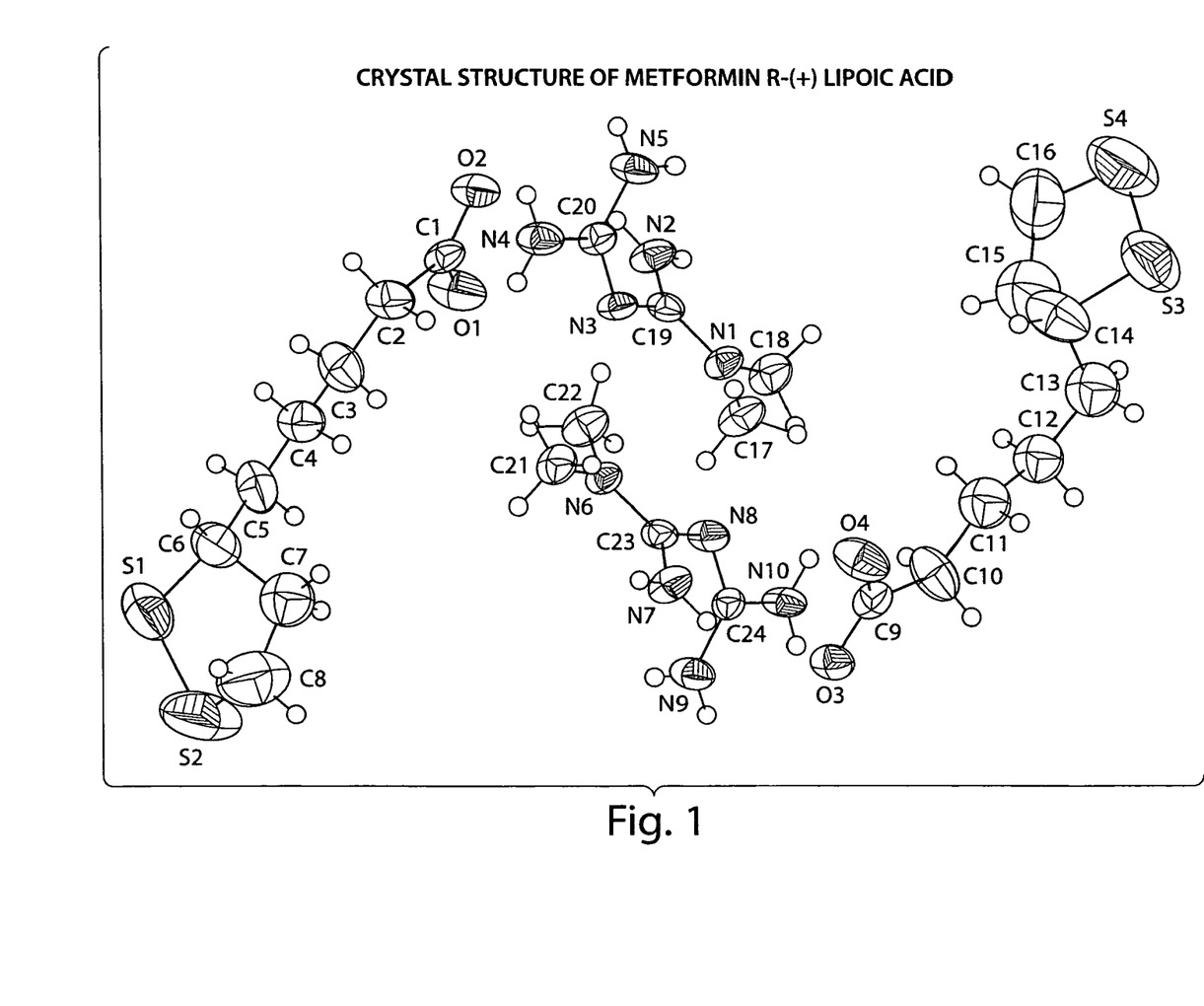
FIG. 1. Crystal structure of metformin R-(+)-lipoate, as described in Example 7.

| Crystal data and structure refinement for metformin R-(+) lipoate | |
|---|---|
| Empirical formula: | $C_8H_{13}O_2S_2^- \cdot C_4H_{12}N_5^-$ |
| Formula weight: | 335.49 |
| Temperature: | 294(2) K |
| Wavelength: | 0.71073 Å |
| Crystal system, space group: | Monoclinic, P2$_1$ |
| Unit cell dimensions: | a = 13.4597(16) Å α = 90° |
| | b = 8.9442(11) Å β = 104.516(2)° |
| | c = 14.5332(17) Å γ = 90° |
| Volume: | 1693.7(4) Å$^3$ |
| Z, Calculated density: | 4, 1.316 Mg/m$^3$ |
| Absorption coefficient: | 0.326 mm$^{-1}$ |

| Crystal data and structure refinement for metformin R-(+) lipoate | |
|---|---|
| F (000): | 720 |
| Crystal size: | 0.18 × 0.15 × 0.06 mm |
| θ range for data collection: | 1.45 to 25.00° |
| Limiting indices: | −16 <= h <= 16, −10 <= k <= 10, −17 <= l <= 17 |
| Reflections collected/unique: | 16237/5966 [R(int) = 0.0430] |
| Completeness to θ = 25.00: | 100.0% |
| Absorption correction: | None |
| Refinement method: | Full-matrix least-squares on F$^2$ |
| Data/restraints/parameters: | 5966/14/379 |
| Goodness-of-fit on F^2: | 1.038 |
| Final R indices [I > 2σ(I)]: | R1 = 0.0691, wR2 = 0.1528 |
| R indices (all data): | R1 = 0.1034, wR2 = 0.1695 |
| Absolute structure parameter: | 0.11(14) |
| Largest diff. peak and hole: | 0.342 and −0.285 e.Å$^{-3}$ |

Sample Analysis

Products of Examples 1-6 were analyzed for purity using the HPLC method, which is described below:

An Agilent 1100 series LC system (Agilent Technologies) equipped with degasser (G1379A), binary pump (G1312A) and colcom (G1316A) along with auto sampler (G1313A) was used to inject 15 μL aliquots of sample on a Agilent Eclipse XDB-C18, 4.6×150 mm, 5 μm column, maintained at a temperature of 45° C. The mobile phase is water and 95% acetonitrile in water.

The mobile phase was delivered at 0.8 mL/min in the following gradient: 0-4.0 mins-100% water, 4.0-10.0 mins 100-0% water, 10-17 mins 0% water and 17-18 mins 0-100% water. Quantitation was achieved by ELSD detection using PL-ELS 2100 system (Polymer Labs).

Chiral purity of R and S metformin lipoates were determined chromatographically using a chiral stationary phase column (Chiral AGP, Chromtech Ltd.). The lipoates were hydrolyzied and analyzed for the entiomeric excess of lipoic acid formed. The purity of metformin R-lipoate as deduced from this method was in general >98%.

Sample preparation: 2 mg of metformin R-(+)-lipoate was dissolved in 1 mL water for analysis using HPLC.

Chromatographic Conditions:

Equipment: Agilent HPLC with DAD Detector, binary pump, auto injector, column thermostat and suitable data processor.

| Method of analysis | |
|---|---|
| Detection | DAD; wavelengths: 210, 225 |
| Column | Chiral AGP 100 × 4.0 mm × 5 μm. (Chrom Tech Ltd) |
| Column temperature | 25° C. |
| Flow Rate | 0.9 mL/min. |
| Injection volume | 20 μL |
| Mobile Phase | −0.01M Sodium dihydrogen Phosphate buffer (pH = 5.0, adjusted with Phosphoric acid) containing 9% Isopropanol. |
| Lipoic acid Sample preparation | Dissolve 1 mg of Lipoic acid in 1 mL of methanol and dilute with 10 mL mobile phase. |
| IG MD009 sample preparation | Dissolve 1 mg of IG MD009 in 1 ml water and dilute with 10 ml mobile phase. |

Example 8

Animal Models To Determine the Biological Effects of Metformin (R)-(+) Lipoate

Diabetic Rats Model:

This example describes diabetic rat model useful for determination of conditions leading to a method for treatment and prevention of post-ischemic damage of the heart and heart tissue.

Spontaneously diabetic Bio-Bred (BB/W) rats from the colony maintained at the University of Massachusetts Medical Center, Worcester, are used in this study. BB/W rats are chosen for the current study because the BB/W rats are considered a useful model of autoimmune human insulin-dependent diabetes (IDDM). Like human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves are all well documented in BB rats; this is described in Diab. Metab. Rev., 8:9 (1992). The BB/W rats are 3-4 months old and weigh between 300-350 g. The BB/W rats receive daily insulin, which is discontinued 24 hours prior to performing the isolated heart perfusion studies, leading to a hyperglycemic state. These rats are acutely diabetic, receiving 2.02+0.04 units of insulin daily, and have been diabetic for at least 12±3 days. The mean blood glucose levels in these diabetic rats are 386±24 mg/dL. The age-matched non-diabetic controls have mean blood glucose levels of 92±12 mg/dL.

Isolated Perfused Heart Model:

This example describes an isolated perfused rat heart model useful in development of this invention.

Studies are performed using an iso-volumic isolated rat heart preparation. Acutely diabetic male BB/W rats and non-diabetic age-matched (3-4 months old) control are pretreated with heparin (1000 u; IP), followed by sodium pentobarbital (65 mg/kg; IP). After deep anesthesia is achieved as determined by the absence of a foot reflex, the hearts are rapidly excised and placed into iced saline. The arrested hearts are retrograde perfused in a non-recirculating model through the aorta within 2 minutes following their excision. Left ventricular developed pressure (LVDP) is determined using a latex balloon in the left ventricle with high pressure tubing connected to a pressure transducer. Perfusion pressure is monitored using high pressure tubing off the perfusion line. Hemodynamic measurements are recorded on a 4-channel Gould recorder. The system has two parallel perfusion lines with separate oxygenators, pumps and bubble traps, but common temperature control allowing rapid change perfusion media. The hearts are perfused using an accurate roller pump. The perfusate consists of (in mM/L) NaCl 118, KCl 47, CaCl$_2$ 12, MgCl$_2$ 12, NaHCO$_3$ 25, and the substrate 11 mM glucose. The perfusion apparatus is tightly temperature controlled, with heated baths being used for the perfusate and for the water jacketing around the perfusion tubing to maintain heart temperature at 37°±0.5° C. under all conditions. The oxygenated perfusate in the room temperature reservoir is passed through 25 feet of thin-walled silicone tubing surrounded by distilled water at 37° C. saturated with 95% oxygen. The perfusate then enters the water jacketed (37° C.) tubing leading to the heart through a water-jacketed bubble trap. This preparation provides excellent oxygenation that routinely is stable for 3-4 hours.

Model For Zero-flow Ischemia:

Diabetic control (DC), diabetic treated (DZ), normal, control (C) and normal treated (CZ) hearts are subjected to 20 minutes of normoxic perfusion followed by 20 minutes of zero-flow ischemia where the perfusate flow is completely shut off, followed by 60 minutes of reperfusion. Hearts are treated with 1 micro Molar metformin R-(+)-lipoate. In the metformin R-(+)-lipoate treated diabetic group (DZ), hearts are subjected to 10 minutes of normoxic perfusion with normal Krebs-Henseleit buffer and 10 minutes of normoxic perfusion with Krebs-Henseleit buffer containing 1 micro Molar metformin R-(+)-lipoate.

The hearts are then subjected to 20 minutes of zero-flow ischemia followed by 60 minutes of reperfusion. In order to avoid any variability in reperfusion conditions, both DC and DZ hearts are reperfused with normal Krebs-Henseleit buffer.

Model For Low-flow Ischemia:

Diabetic control hearts (DC) are subjected to 20 minutes of normoxic perfusion at a flow rate of 12.5 ml/min followed by 30 minutes of low-flow ischemia where the perfusate flow is slowed down to 1.25 ml/min, that is about 10% of normal perfusion, followed by 30 minutes of reperfusion at a normal flow rate (12.5 mL/min).

In the metformin R-(+)-lipoate treated diabetic or non-diabetic groups (DZ or CZ), hearts are subjected to 10 minutes of normoxic perfusion (flow rate 12.5 mL/min) with normal Krebs-Henseleit buffer and 10 minutes of normoxic perfusion with Krebs-Henseleit buffer containing 1 micro Molar metformin R-(+)-lipoate. The hearts are subjected to 30 minutes of low-flow ischemia (flow rate 1.25 mL/min) and 30 minutes of reperfusion at normal flow rate (12.5 mL/min).

Animal models to determine the effects of compounds and compositions as disclosed herein on diabetes and complications of diabetes have been reviewed by Tirabassi et al., *ILAR Journal*, 2004, 45, 292-302. Antidiabetic activity of compounds of Formula I can also be tested according to protocols described in the following patents: U.S. Pat. Nos. 4,340,605; 4,342,771; 4,367,234; 4,617,312; 4,687,777 and 4,703,052. Erythrocyte GSH levels in diabetic patients can be measured according to Murakami et al., as described in *Metabolism*, 1989, 38, 753-758. Additional references relevant to this application include the following: French Patent, 2796551 (Jan. 26, 2001)) and US Patent Application No. 2003-0220301(Nov. 27, 2003).

It should be understood that the invention is not limited to the particular embodiments described herein, but that various changes and modifications may be made without departing from the spirit and scope of this invention as defined by the following claims.

The journal articles, scientific references, and patent publications cited above are incorporated herein in their entirety by reference.

The invention claimed is:

1. A compound having a structure of formula I, which is metformin R-(+) lipoate, or a pharmaceutically acceptable solvate or hydrate thereof, wherein the said compound is a crystalline solid as determined by single crystal X-ray diffraction and depicted in FIG. 1

-continued

2. A compound having a structure of formula I, which is metformin R-(+) lipoate, or a pharmaceutically acceptable solvate or hydrate thereof, wherein the said compound shows an X-ray powder diffraction diagram as depicted in FIG. 2

(I)

3. A pharmaceutical composition, comprising the compound according to claim 1 and a pharmaceutically acceptable carrier, vehicle or diluent.

4. A pharmaceutical composition, comprising the compound according to claim 2 and a pharmaceutically acceptable carrier, vehicle or diluent.

5. A kit comprising
a) a unit dosage form comprising a compound according to claim 1 or 2, or a pharmaceutically acceptable salt thereof;
b) instructions on how to use the kit; and
c) at least one container for holding the unit dosage forms.

6. A method for treating diabetes in a mammal, comprising administering a therapeutically effective amount of the compound according to claim 1.

7. A method for treating diabetes in a mammal, comprising administering to said mammal a therapeutically effective amount of the mixture compound according to claim 2.

8. A method for treating a diabetic complication in a mammal, comprising administering a therapeutically effective amount of the compound according to claim 1.

9. The method according to claim 8, wherein said diabetic complication is selected from nephropathy, neuropathy, retinopathy, cataracts, cardiomyopathy and heart tissue ischemia.

10. A method for treating a diabetic complication in a mammal, comprising administering to said mammal a therapeutically effective amount of the compound according to claim 2.

11. The method according to claim 10, wherein said diabetic complication is selected from nephropathy, neuropathy, retinopathy, cataracts, cardiomyopathy and heart tissue ischemia.

12. A composition comprising the compound of claim 1 or 2, which composition has a purity of greater than 95%.

13. The composition of claim 2, which has a purity of greater than 98%.

14. The composition of claim 12, which has a purity of greater than 99%.

* * * * *